United States Patent [19]

Strand et al.

[11] Patent Number: 5,133,355
[45] Date of Patent: Jul. 28, 1992

[54] BIOMEDICAL ELECTRODE CONSTRUCTION

[75] Inventors: Jerome E. Strand, Hudson, Wis.; Lawrence W. Craighead, Mendota Heights; Clarence A. Niven, White Bear Lake, both of Minn.

[73] Assignee: Minnesota Mining and Manufacturing Company, St. Paul, Minn.

[21] Appl. No.: 788,192

[22] Filed: Nov. 5, 1991

Related U.S. Application Data

[62] Division of Ser. No. 534,161, Jun. 6, 1990, Pat. No. 5,078,139, which is a division of Ser. No. 247,707, Sep. 22, 1988, abandoned.

[51] Int. Cl.⁵ .......................................... A61B 5/0402
[52] U.S. Cl. .................................................. 128/640
[58] Field of Search ........................... 128/639–641, 128/644, 798, 802, 803

[56] References Cited

U.S. PATENT DOCUMENTS

| | | | |
|---|---|---|---|
| 1,662,446 | 3/1928 | Wappler | 128/798 |
| 3,187,745 | 6/1965 | Baum et al. | 128/639 |
| 3,340,868 | 9/1967 | Darling | 128/640 |
| 3,888,240 | 6/1975 | Reinhold, Jr. et al. | 128/644 |
| 4,166,465 | 9/1979 | Esty et al. | 128/798 |
| 4,522,211 | 6/1985 | Bare et al. | 128/640 |
| 4,539,996 | 9/1985 | Engel | 128/798 |
| 4,643,193 | 2/1987 | DeMarzo | 128/639 |
| 4,657,023 | 4/1987 | Kuhn | 128/640 |
| 4,679,563 | 7/1987 | Wada et al. | 128/640 |
| 4,694,835 | 9/1987 | Strand | 128/640 |
| 4,715,382 | 12/1987 | Strand | 128/640 |
| 4,852,571 | 8/1989 | Gadshy et al. | 128/640 |
| 4,922,911 | 5/1990 | Wada et al. | 128/640 |

FOREIGN PATENT DOCUMENTS 1519782  8/1978  United Kingdom ............... 128/640

OTHER PUBLICATIONS

Medical Instrumentation, Webster, pp. 245–247, 1978.

Primary Examiner—Lee S. Cohen
Attorney, Agent, or Firm—Gary L. Griswold; Walter N. Kirn; John H. Hornickel

[57] ABSTRACT

A biomedical electrode is disclosed which generally comprises an insulator construction and a conductor member. The conductor member is preferably a thin flat, flexible member having a pad portion and a tab portion. The insulator construction is arranged such that the conductor member pad portion is positioned on one side of the insulator construction and the tab portion is generally positioned on an opposite side. Three general embodiments are disclosed which achieve this: a first comprising two overlapping sections of insulator material, with the tab portion of the conductor member extending outwardly from therebetween; a second in which two sections of insulator construction material are oriented in a substantially coplanar relationship to define a seam therebetween, through which a portion of the conductor member extends; and, a third in which the insulator construction includes a single sheet of material having a slot therein, through which a portion of the conductor member extends. For any of those three embodiments, a substantially flat arrangement results, with advantages associated therewith. Preferred arrangements having a field of conductive adhesive, associated with the pad portion of the conductor member, completely surrounded by a border of insulator construction and skin adhesive, are described.

9 Claims, 3 Drawing Sheets

BIOMEDICAL ELECTRODE CONSTRUCTION

This is a division of application Ser. No. 07/534,161, filed June 6, 1990, now U.S. Pat. No. 5,078,139, which is a division of application Ser. No. 07/247,707, filed Sept. 22, 1988, now abandoned.

FIELD OF THE INVENTION

The present invention relates to biomedical electrodes. More specifically, the invention concerns a preferred electrode construction for application to a skin surface of a subject to be evaluated, for example a human subject. The invention particularly concerns such an arrangement which is flexible in construction and presents a relatively low relief, to advantage.

BACKGROUND OF THE INVENTION

Electrocardiography is the well-established, but still rapidly developing, science of making and studying graphic records (electrocardiograms) generated by electrical currents originating in the heart. The technology is readily applicable in both human and veterinary medicine and, while the focus of attention in the present specification will be on human medicine, it will be understood that many of the techniques described, including the present invention, are applicable in some forms of veterinary medicine as well.

An electrocardiogram (ECG) is measured through utilization of an electrocardiograph instrument, which monitors the electric potentials associated with those electric currents that transverse the heart. In practice, electrodes are positioned on the skin surface of the subject to be evaluated; those electrodes being in electrical communication with the electrocardiograph instrumentation. The electrodes must generally be such as can accurately detect and transmit electrical signals produced by various biological events. This generally requires: a large conductive surface for receipt of electrical signal; a good conductive interface between a conductor (conductive surface) and the patient; and, a secure affixation of the electrode to the subject, to avoid relative movement between the subject and the electrode during monitoring.

Electrocardiography has been applied in a variety of circumstances including: in resting diagnostic procedures; in surgical and emergency room procedures; in cardiac units; in critical care units; in ambulatory monitoring; in stress diagnostic procedures; and, more recently, in providing either continual, or intermittent, monitoring as selected for a person not under constant supervision and not substantially restrained with respect to activity. With respect to this latter application, the subject is generally provided with a portable monitor, such as a belt monitor, in electrical communication with a plurality of electrodes attached to the subject's body. An example of this is the Holter monitoring system.

Unique problems arise when the application of electrocardiography is to a subject who is expected to be monitored during more or less normal, substantially non-restricted, activity or behavior. The following list is a non-exhaustive discussion of some of these unique problems or circumstances.

1. Such subjects must be expected to undergo their normal daily routines fully clothed. Thus, the electrode system must be one such as will not be likely to be readily interfered with by clothing or the like. Further, a skin-adhesive and/or electrolyte solution or conductive adhesive utilized in association with the electrodes should be sufficiently retained (enclosed) by the electrode to inhibit likelihood of contact with the subject's clothing, for aesthetic reasons, to avoid damage to the clothing, and for comfort and convenience. Further, subjects will generally prefer arrangements which have a relatively low relief or profile, and will be thus substantially inconspicuous when worn.

2. The subject may engage in substantial movement during monitoring. To avoid interference with electrical signals measured, it is important to avoid substantial relative movement between the subject and the electrode. This generally requires an electrode which can readily flex, as the subject's body moves or twists. Further, it generally requires an arrangement which can insure a secure, relatively long-lasting, adhesion and contact between the subject's body and the electrode.

3. In use, the electrode will be attached by means of a coupler arrangement to wire leads extending into communication with the electrocardiograph. In some instances, these leads may be attached and detached a number of times during monitoring.

Several types of features and/or capabilities are desirable in arrangements well-adapted for use under such circumstances. The following list is a non-exhaustive presentation of such features and/or capabilities.

1. Preferably, the arrangement includes features which facilitate ease of good, secure, conductive connection to an electrocardiograph lead.

2. It is desirable that the device include features which facilitate connection to a monitor without application of significant deleterious stress to the adhesive interface between the electrode and the subject.

3. Preferably, features are provided which allow for a plurality of cycles of connection and disconnection, without a substantial likelihood of failure of electrode components. However, it is noted that in many home use situations, disattachment of the leads will probably be discouraged by prescribers of the procedure.

4. For good operation, it is important to provide an appropriate conductive interface between the electrode and the subject's body. In general, this is provided either by use of an electrolyte gel or through use of a conductive adhesive positioned between a conductive portion of the electrode and the subject's body. If the electrode is to be maintained in position on the subject's body, in the absence of continuous supervision by medical personnel and for a substantial length of time, it is preferred that:

a) the electrode construction be such that substantial leakage of the electrolyte gel and/or the conductive adhesive outwardly from between the subject's body and the electrode is avoided or at least substantially inhibited; and, b) entry of foreign material, for example water or dirt, which can interfere with the electrolyte gel and/or conductive adhesive, into the interface between the electrode and the subject's body is substantially inhibited.

5. Persons wearing electrocardiograph electrodes for a substantial period of time, and during periods of normal living activity, can be expected to bring the surface of their bodies, in the vicinity of the electrodes, into contact with water. For example, the person may become wet due to weather, normal bathing activities, or spills from accidents. This can interfere with electrodes in numerous manners. For example:

a) the water could lead to signal artifact (noise);

b) the water can cause deterioration in electrode components; and, c) the water can cause deterioration of the adhesive interface between the electrode and the person's skin, should the water leak thereto. It is preferred that the electrode be constructed in a manner resistent to such damage from water.

6. Ends of the leads attachable to the electrodes, in order to provide communication with the electrocardiograph monitor, will include electrically conductive portions at least partially exposed thereat. It is desirable to provide an arrangement in which it is unlikely that, even during subject movement, these electrically conductive portions on the leads will: come into direct contact with a subject's body; come into direct contact with electrolyte gel and/or conductive adhesive; and/or come into contact with adjacent leads and/or electrodes.

7. During normal subject movement, it can be expected that substantial tugging on the leads may occur. For example, as the subject moves or bends and the leads might be pulled tight. This may cause a tugging on the electrodes, applying stress to the adhesive interface between the electrode and the subject's body. It is desirable to provide an arrangement which substantially and efficiently avoids the likelihood that such stress will separate the electrode from the patient's body.

8. In general, it is a preferred practice to dispose of biomedical electrodes after use, particularly after an unsupervised, outpatient, use. This generally requires electrodes which can be relatively inexpensively and efficiently constructed. It is also desired that the electrodes be of a design which includes relatively inexpensive components that can be easily assembled utilizing mass manufacturing techniques.

9. It is foreseeable that subjects wearing biomedical electrodes and engaging in normal living activities may accidentally be bumped or jostled in a manner making contact between the immediate vicinity of the biomedical electrode and some foreign object. Further, a wearer of the electrode on his or her chest, may decide to lie flat on his or her stomach. It is desirable that the biomedical electrode be constructed in such a manner that it is unlikely to be damaged by such contacts or pressure. Further, it is desirable that the biomedical electrode not include hard, projecting, portions which would cause a bruise to a wearer's body, as a result of such contacts or pressure.

10. Persons wearing biomedical electrodes may be subjected to examinations such as X-ray evaluations. It is desirable that the biomedical electrode be such that it will not be likely to cause a problem shadow on a developed X-ray image, or similar image. That is, any image made by the electrode will be relatively faint and non-interfering with interpretation.

11. It can be foreseen that those portions of the electrode which are engaged by a clip or the like in communication with the monitor will be intermittently, but repeatedly, manipulated. Such manipulations of a component of the electrode can lead to a failure of the arrangement, for example by an undesired pulling at seams of the arrangement, or in similar manners. It would in general, be preferred that the biomedical electrode be designed such that manipulation of a portion thereof which is engaged by a clip or lead in communication with the monitor, is unlikely to result in an undesired or premature failure of the system.

12. Further, manipulation of portions of the electrode may tend to cause an "edge lift" effect; that is portions of the outer periphery of the electrode may be lifted from the subject's skin. This can lead to problems with: signal artifact (noise); contamination of conductive adhesive, etc. Preferably the construction of the electrode is such as will minimize, or at least inhibit, the likelihood of such edge lift.

The above list generally defines those features and capabilities it is desirable to have provided by a biomedical electrode construction. It will be understood that the list is not intended to be exhaustive, but rather it is to be interpreted as generally instructional, as to the background of biomedical electrodes. In general, a wide variety of biomedical electrodes have been provided, some of which address some or all of the above-described features and needs with varying degrees of success. No conventional biomedical electrode construction is fully satisfactory with respect to all of these problems and concerns, and improvements are continually being sought. It is an object of the present invention to provide a biomedical electrode construction which is improved over many conventional electrode arrangements, with respect to its performance in providing for the above-recited features and/or in addressing the recited problems.

SUMMARY OF THE INVENTION

The present invention concerns a preferred biomedical electrode arrangement for use in electrocardiography. Electrodes according to the present invention include: a flexible insulator construction; and, a substantially flat, flexible, conductor member. These elements are arranged in a preferred manner to provide for desirable characteristics and advantages.

More specifically, the conductor member includes a pad portion and a tab portion. The pad portion is arranged and oriented to receive electrical signals from the subject's body. The tab portion, on the other hand, is available for engagement with a wire lead or the like, to provide electrical communication to an electrocardiograph monitor.

According to the present invention, the conductor member is oriented, relative to the insulator construction, such that the pad portion of the conductor member is positioned on a first side of the insulator construction, and the tab portion is positioned on a second, opposite, side of the insulator construction. In three preferred embodiments described in detail below, this is accomplished in various manners.

In the first, preferred, embodiment, the insulator construction includes first and second sections of substantially non-conductive material. Each section has an edge portion which includes a border portion. The electrode is oriented with the first and second sections positioned substantially coplanar with one another, and with the edge portions opposed to, and in an overlapping relationship with, one another. The conductor member is oriented in this arrangement with the tab portion projecting between the overlapping edge and border portions of the insulator construction sections. This results in the tab portion being oriented generally on one side of the insulator construction, with the pad portion being oriented on the other. Of course, part of the conductor member, typically part of the tab portion, extends between the two sides.

In a second embodiment, the insulator construction again includes first and second sections of non-conductive material, each section having an edge portion. For the second embodiment, the first and second insulator construction sections are oriented substantially coplanar with one another, with the edge portions oriented opposed to one another but in a non-overlapping relationship. That is, the edge portions face one another, defining a seam therebetween. For this embodiment, the conductor member is oriented with the tab portion projecting through the seam defined between the sections. As with the first embodiment, this results in an arrangement having the tab portion generally on one side of the insulator construction, and the pad portion on an opposite side.

To facilitate a seal along the seam between the two sections, a strip of sealant or tape may be used to overlap the tab portion and the extension of the seam. As will be seen from the drawings and detailed descriptions, such an arrangement not only facilitates strength and integrity of the seam, but it also reduces the likelihood of leakage and helps provide a desired support to certain portions of the conductor member.

In the third general embodiment, the insulator construction includes a single section of non-conductive material, having a slit therein. The conductor member is oriented, relative to the insulator construction, such that the tab portion extends through the slit, again leaving an arrangement having the pad portion on one side of the insulator construction and the tab portion on the other side. With this embodiment an optional extension of sealing tape can be used to extend over the slit and the tab portion, to yield advantages generally analogous to those obtained from the second embodiment through use of a similar sealing arrangement.

From the above general constructions, numerous advantages result. For example, due to its flexible construction, the biomedical electrode of the present invention can be easily positioned in engagement with a portion of a subject's body. Should the subject move or twist while the biomedical electrode of the present invention is in position, the electrode can readily flex or bend to accommodate the movement and/or twists of the subject's body.

In addition, as will be seen from the detailed descriptions, such an arrangement is relatively easy to construct. Also, it can be formed from relatively inexpensive materials. Thus, from a cost standpoint, a commercially feasible, disposable, element can be readily created.

In general, and as will be seen from the detailed descriptions, the bulk of the tab portion of the conductor element is left resting against an outside surface of the insulator construction, when a biomedical electrode of any of the preferred embodiments of the present invention is in use. A lead from the electrocardiograph is then attached to the tab portion. Typically, the electrical connection is provided by means of a clip or clasp element which can be attached to the conductor member tab portion. Due to the arrangement described, the clip or clasp, having electrically conductive elements therein, is insulated from direct contact with the subject's body, by means of the insulator construction. That is, it is unlikely that the clip or clasp will receive electrical signals other than through the conductive member. As a result, the arrangement of the present invention provides for relatively low likelihood of unintended noise interrupting the desired signal to be received by the electrocardiograph monitor. It will be seen, from the detailed description and drawings, that for the preferred embodiments such an insulation of the clip or clasp from the subject's body is achieved in a secure manner; and, if desired, even in the absence of adhesive tape or the like being used to maintain or retain the clip in position. This facilitates attachment and detachment of the clip as necessary, and further facilitates subject comfort.

In general, for attachment to a subject's body, skin adhesive is applied to the first side of the insulator construction. The biomedical electrode is then adhesively secured to a subject during use, with conductive adhesive or gel between the pad portion and the skin of the subject. It will be understood from the drawings that this results in an arrangement having the relatively flat conductive member extending substantially parallel to the insulator construction and the subject's body. Thus, the greatest component of any typical force directed against the conductive member, by means of a typical tugging on the clip and leader lines, will likely be directed as a shear force operating of the interface between the conductive pad/insulator construction arrangement, and the subject's body. Since the arrangement directs the force in such a manner, the tugging force is not very likely to result in separation of the biomedical electrode from the subject's body. Alternately, a force including a substantial component directed otherwise might have a tendency to separate the biomedical electrode from the subject's body. The construction of the invention is advantageous, since it directs the typical tugging force in a preferred manner. That is, the typical tugging force is converted to a shear force which is unlikely to result in a failure at the adhesive interface between the subject and the electrode. In some conventional electrodes, the construction allows for a substantial development of a force of separation, and a concomitant likelihood of adhesive failure.

As will be seen from the detailed descriptions, biomedical electrodes according to the above-described description, and in accordance with preferred embodiments of the present invention, include no components which can form hard projections, likely to hurt or bruise a wearer, should the wearer be accidentally bumped in the vicinity of the biomedical electrode or lie down on top of the electrode. Further, the relatively flat components are unlikely to be damaged by such activities.

In a prefered embodiment, electrical contact between the conductive member pad portion and the subject's body is maintained by means of a conductive adhesive or gel. Preferably the insulator construction is sized, relative to the conductor member pad portion, so as to define a border portion of insulator construction which extends completely around an outer perimeter of the conductive member pad portion. That is, the gross surface area of the conductor member pad portion is smaller than the gross surface area of the insulator construction first side, and the insulator construction first side acts as an overlapping backing to the conductor member pad portion. In general, this results in an arrangement in which at least some of the skin adhesive will form a border extending completely around the conductive adhesive or gel. Thus, the skin adhesive can be used to insulate or separate the conductive adhesive or gel from edges of the biomedical electrode.

Several advantages result from this. First, the likelihood of exposure of the conductive adhesive or gel to the elements is lessened. Thus, deterioration in performance of the conductive adhesive or gel is inhibited.

Further, it will be less likely that the conductive adhesive or gel can leak in a manner causing undesired signal artifact.

Also, typical pressure-sensitive skin adhesives, which do not need to be electrically conductive, generally are considerably longer lasting and have a stronger propensity to adhere, than do conventional conductive adhesives or electrolyte gels. As a result, edges of the biomedical electrode (held in place by skin adhesive rather than conductive adhesive) will be less likely to lift up in time and thus allow for possible leaks to, or contamination of, the area in the immediate vicinity of the conductive member pad portion. Good sealing is particularly desirable for electrodes which are intended to be used by outpatients, over considerable periods of time, since the patient will likely move considerably, and perhaps even bathe, with the electrode in position.

Substantially flat conductive members according to the present invention can be formed from a relatively thin layer of flexible polymeric material, such as a polyester film, having a conductive layer, such as a silver/silver chloride material, on at least one side thereof. Preferred such materials, being relatively thin, are very flexible, and can be readily and easily mounted in the arrangements required by the invention. Further, they are relatively transparent to X-ray, so a person wearing biomedical electrodes according to preferred embodiments of the present invention can be examined by X-ray without significant problems from strong shadows. That is, the person need not be bothered by removal and remounting of the biomedical electrodes, in order for routine X-ray examinations or the like to occur.

In general, for each of the three embodiments the tab portion of the conductive member extending outwardly along an outside or front side of the insulator construction will tend to act as a flap which, if pulled in an appropriate direction, operates against the contact between the conductive member pad portion and the subject's body. Further, in some embodiments movement of the tab portion can: tend to facilitate failure of the integrity of the biomedical electrode; cause undesired noise to be received by the electrocardiograph monitor; or, generate a site at which conductive material, such as conductive adhesive and/or electrolyte gel, can leak out from between the conductive member pad portion and the wearer's body. To inhibit the tab portion from causing such problems, in preferred embodiments of the present invention a segment or portion of the tab portion located substantially adjacent or proximal to the pad portion is secured in position by means of an adhesive or the like. Various arrangements are possible, in part depending upon the embodiment of the application. For example, a strip of adhesive tape may be applied across an outer surface of the tab portion, securing it in position against the insulator construction. Alternatively, an adhesive can be positioned between the tab portion and a side of the insulator construction, to similarly effect a sealing engagement.

In general, when first manufactured the biomedical electrode will include a protective release liner or the like secured to the first side of the insulator construction. The release liner can be selectively separated from the insulator construction first side, to expose the skin adhesive and conductive adhesive (or electrolyte gel). A variety of materials may be utilized as a release liner, for example a silicone coated polypropylene material might be utilized. In preferred embodiments, a spacer or tab positioned between a portion of the release liner and the insulator construction can be used to facilitate separation.

In typical embodiments of the skin adhesive will completely cover the first side of the insulator construction, and the conductive adhesive will be applied as a pool or field in a central portion of the field of skin adhesive. Conventional conductive adhesives may not adhere well to the non-conductive pressure-sensitive adhesive of the biomedical electrodes. If, in the embodiment of application, such is the case, then a scrim may be positioned between the conductive adhesive and the non-conductive skin adhesive, to facilitate adherence. That is, a thin layer of material may be utilized as the bridge between the conductive adhesive and the non-conductive skin adhesive.

The drawings constitute a part of this specification and represent preferred embodiments of the invention. It will be understood that, in some instances, relative component sizes and/or material thicknesses may be shown exaggerated, to facilitate an understanding of the invention.

BRIEF DESCRIPTION OF THE DRAWINGS

FIG. 6 including a release liner not shown in FIG. 5.

FIG. 7 including an optional strip of sealing tape on an upper portion thereof.

FIG. 8 not showing the optional strip of tape of FIG. 7, but showing a release liner.

DETAILED DESCRIPTION OF PREFERRED EMBODIMENTS

Detailed descriptions of certain embodiments of the present invention are provided hereinbelow. It is to be understood that the embodiments described and shown are representative only, and that the present invention may be embodied in various forms not depicted or specifically described in detail.

Figure 1:
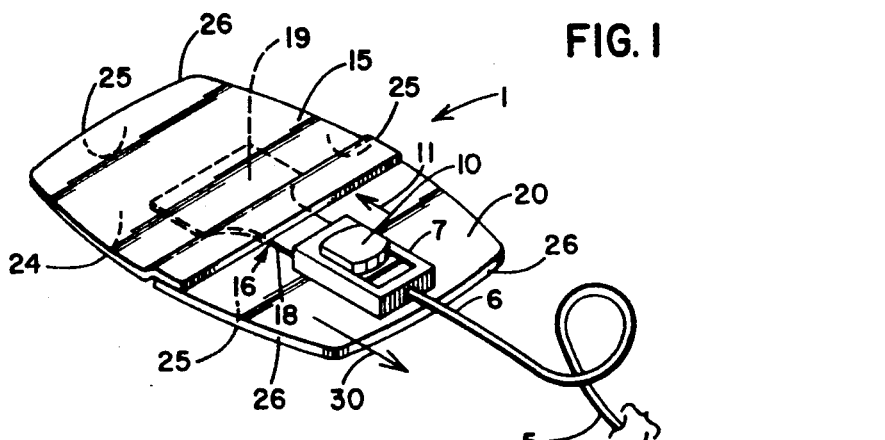
FIG. 1 is a perspective view of a biomedical electrode according to the present invention, shown in an environment of association with an electrocardiograph monitor and with a lead extending from the electrode to the monitor, phantom lines indicating a portion of the electrode hidden from view.

The reference numeral 1, FIG. 1, generally designates a biomedical electrode according to a first embodiment of the present invention. The electrode 1 is depicted in perspective, and is shown in association with an electrocardiograph monitor 2. It will be understood that monitor 2 may be a portable, belt-type monitor, as shown. That is, electrodes such as electrode 1 according to the present invention include features particularly well adapted for use with subjects who are not expected to be substantially restricted and who are expected to utilize the biomedical electrodes over a substantial period of time. For example, electrodes 1 according to the present invention may be utilized by outpatients, wearing belt-type monitors 2 typically for about a day. Biomedical electrodes such as electrode 1 may be used with a variety of types of monitors 2, including non-portable ones.

Electrical communication between electrode 1 and monitor 2 is generally provided by means of a lead 5 having a first end 6 attached to a clip or clasp 7, and a second end 8 attached to a jack 9 or the like, for engagement with monitor 2. A variety of clips 7 may be utilized. The one shown in FIG. 1, includes a thumb operated cam 10 which, when slid in the direction indicated by arrow 11, causes gripping of a thin, flat member, in particular a tab portion of electrode 1 described below.

Electrodes 1 according to the present invention include two primary components: a flexible insulator construction 15; and, a substantially flat, flexible, conductor member 16. A preferred association between conductor member 16 and insulator construction 15 yields many of the advantages of the present invention.

Still referring to FIG. 1, conductor member 16 generally includes a tab portion 18 and a pad portion 19. According to the present invention, the conductor member 16 is oriented relative to the insulator construction 15 such that the pad portion 19 is on one side (i.e. a first side) of the insulator construction 15 and the tab portion 18 is generally on an opposite side of the insulator construction 15. In FIG. 1, this is represented by a presentation of the pad portion 19 in phantom lines underneath insulator construction 15, whereas part of the tab portion 18, shown in solid lines, is depicted as above surface or side 20 of insulator construction 15. It is noted that tab portion 18 of conductor member 16 includes that portion of the conductor member 16 engagable by clip 7. Typically, for preferred embodiments, the tab portion 18 will be a rather elongate, narrow, extension of conductor member 16.

The pad portion 19 of conductor member 16 is that portion of the conductor member 16 which receives electrical signals from the subject's body. In general, it is preferred that the pad portion 19 be relatively large in gross surface area. The term "gross surface area" used herein is meant to refer to the surface area resulting from the overall outside perimeter dimensions of pad portion 19, and not necessarily to that surface area which can be measured by microscopic examination of the conductor surface of pad portion 19. The term "surface area" or "gross surface area" as used herein in this context is meant to refer to one side only of the pad portion 19. For typical, preferred embodiments of the present invention, to be used as adult human bioelectrodes, the pad portion 19 should have an overall area of about 0.65 to 6.5 cm$^2$. Also, the tab portion 18 should have an overall length of about 2.2-2.6 cm and a width of about 0.8-1.2 cm. It is noted that the pad portions shown in the drawings are roughly 60% wider than they are long, however a variety of sizes and shapes may be used.

In use, conductive material is generally placed between the conductor member pad portion 19 and the user's body. The conductive material is generally either an electrolyte gel, or a conductive adhesive. For preferred embodiments of the present invention, conductive adhesive is used, as it provides not only for good conductive association between the pad portion 19 and the user's body, but it also facilitates adhesion, i.e., maintenance over time of a good association. A variety of conductive adhesives may be utilized, and all that is generally required is that the material function to provide for good electrical contact between pad portion 19 and the subject's body. Preferred conductive adhesives are described in greater detail below.

In preferred embodiments, a side 24 of insulator construction 15 on which the conductor member pad portion 19 is positioned, is substantially larger in surface area than a surface (i.e. one side) of the pad portion 19. Because of this, a border portion 25 is provided, in side 24, which completely surrounds (and backs) pad portion 19 and which allows no substantial gap or passage through electrode. It will be understood that the surface of pad portion 19 referred to in the previous two sentences is generally the first or operative surface for receiving signals, i.e. the surface which faces away from the insulator construction.

In a typical use, a pressure-sensitive skin adhesive is applied at least to the border portion 25 to retain electrode 1 on the body of a user. Any of a wide variety of skin adhesives may be utilized in arrangements according to the present invention. More detail concerning skin adhesives is given below. Typically, the skin adhesive will be applied to all of side 24, with the conductive adhesive and pad portion 19 being positioned thereon.

Numerous advantages result from a border portion 25 which completely surrounds conductor member pad portion 19. First, in general, a good, tight, secure adhesion between electrode 1 and the user's body is facilitated. That is, in use an entire peripheral edge 26 of insulator construction 15 is securely adhered to a user's body, and lift along the edges 26 is unlikely. As a result, the likelihood of contamination of the area in the immediate vicinity of pad portion 19 is significantly reduced. For example, water or other conductive elements will be unlikely to reach pad portion 19 and interfere with electrocardiograph monitoring.

Also, the border 25, with skin adhesive thereon, will completely surround, and tend to retain, any conductor adhesive and/or electrolyte gel positioned in association with pad portion 19. That is, the conductive material will be unlikely to flow outwardly from between pad portion 19 and the user's body. Further, the conductive adhesive and/or electrolyte gel will be less likely to come into contact with deteriorating elements such as water, dirt, soap, etc.

Also in preferred embodiments, surface or side 20 is sized such that the tab portion 18, and any clip 7 in association therewith, is completely insulated or separated from the user's body by the insulator construction 15. That is, surface 20 is sized to provide for a complete backing in overlap of that portion of the tab portion 18 extending outwardly from beneath the insulator construction 15. In this manner, direct contact between clip 7 (and any conductive elements thereon), and the user's body is unlikely. This will inhibit the generation of undesired noise or signals in the system.

The substantially flat construction depicted in FIG. 1 leads to significant advantages. For example, it is foreseen that as the user attaches or detaches clip 7, or goes about ordinary movement with electrode 1 and clip 7 in position, significant tugging or pulling on tab portion 18 may occur. For the most part, due to the flat construction of electrode 1, the major component of this force will typically be directed in the general direction indicated by arrow 30. That is, it will generally be directed parallel to a plane of flat electrode 1 and parallel to the body of a user to which electrode 1 may be attached. This type of force is a shearing force operating on the skin adhesive between insulator construction 15 and the user's body. Since there is relatively little component causing much separation between the two, but rather most of the tugging component will be shear, separation will be less likely to occur. This can be a significant advantage to the present invention, over arrangements wherein a less flat construction is utilized. Alternately phrased, the construction of the electrode 1 is such that typical forces due to tugging on the lead wire 5 are not likely to "lift" the electrode 1 from the subject. Also, the outer peripheral edges of the electrode 1 are isolated from the conductor member 16, so manipulation of the conductor member 16 are unlikely to result in lift along edges of the insulator construction 15, the edges being points of particular likelihood of failure for the skin adhesive.

Another advantage of the rather flat construction is that the electrode 1 will be less conspicuous when worn under the user's clothes. Further, the arrangement can be readily manufactured, manipulated and applied.

It will also be understood that the rather flat, flexible construction does not provide for any substantial projections that might be likely to injure a wearer, should the wearer be bumped in the vicinity of the worn electrode or should the wearer lie down.

Figure 2:
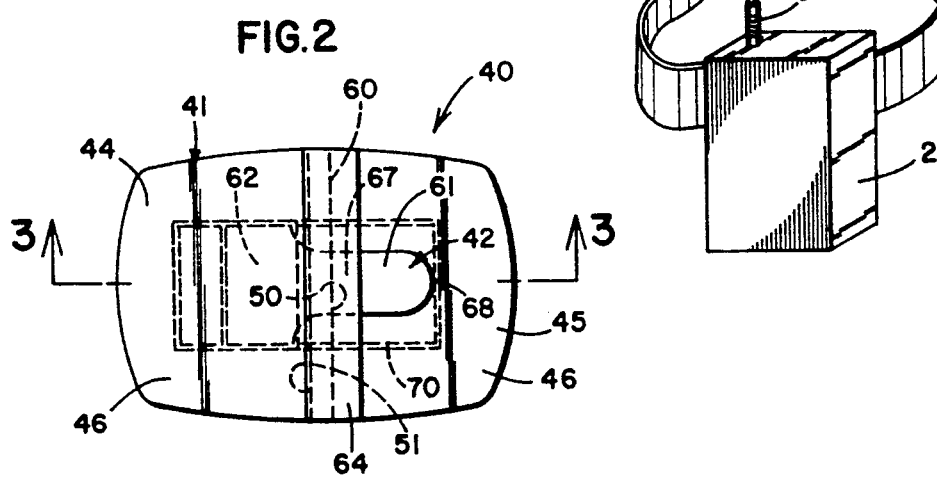
FIG. 2 is a top plan view of a biomedical electrode according to the embodiment of FIG. 1; phantom lines indicating selected portions hidden from view and an optional strip of sealing tape being depicted on top of the electrode.
Figure 3:
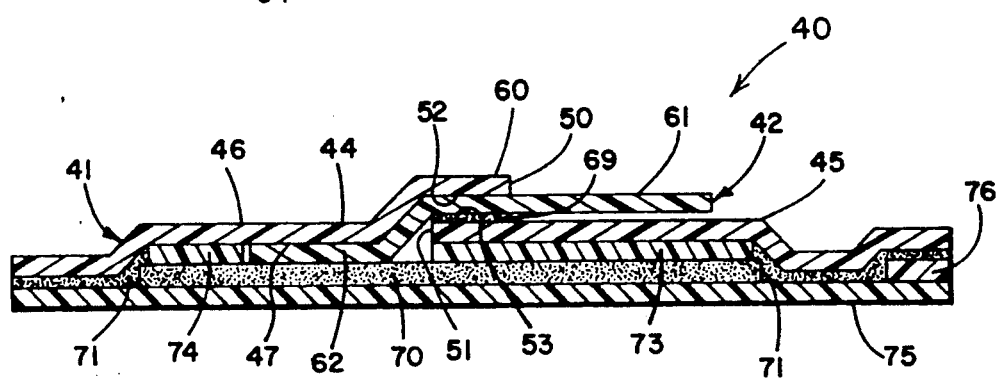
FIG. 3 is an enlarged side cross sectional view taken generally along line 3—3, of FIG. 2, except that FIG. 3 does not include the optional strip of sealing tape shown in FIG. 2, and the device of FIG. 3 does include a release liner.
Figure 4:
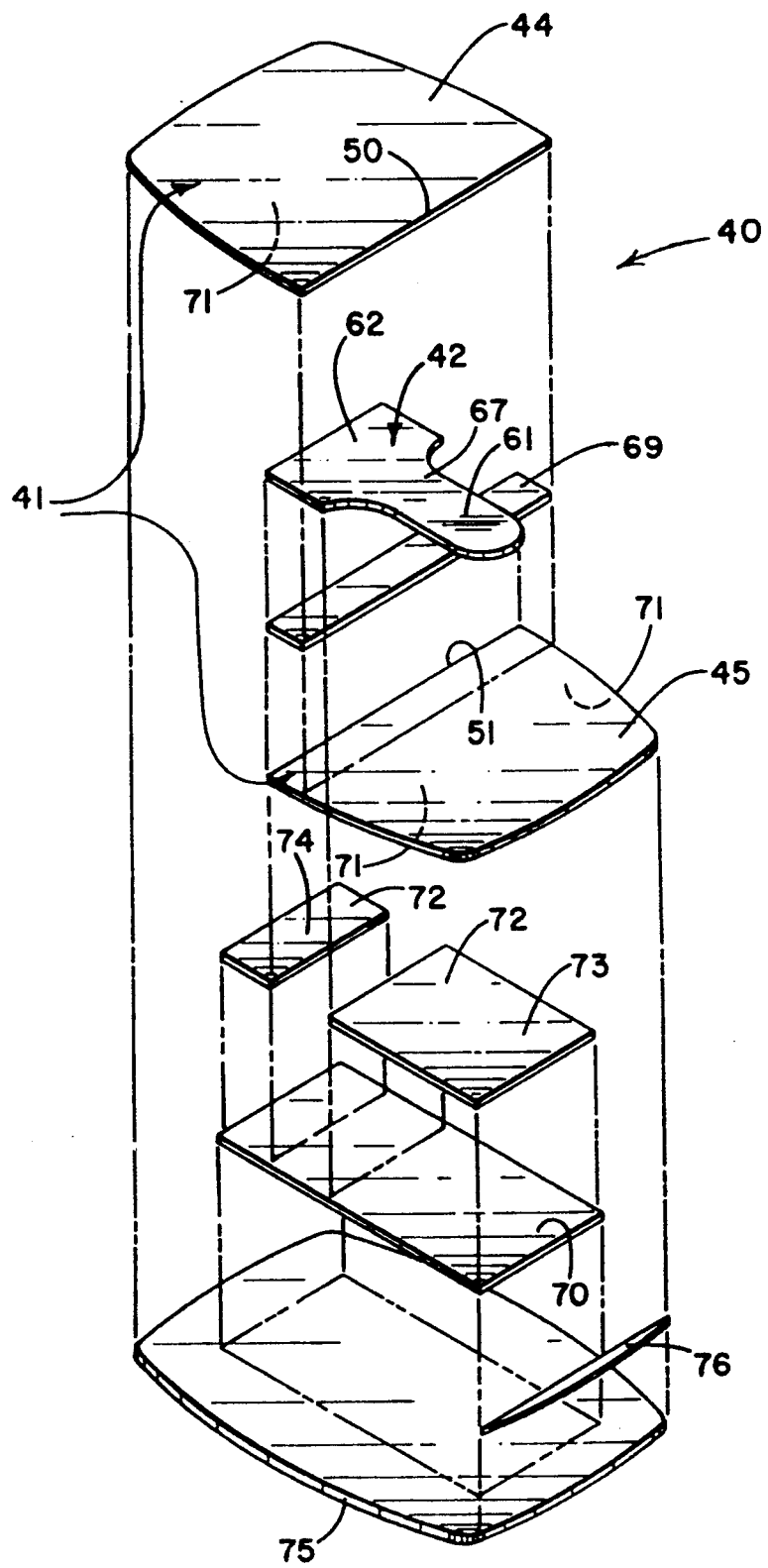
FIG. 4 is an exploded perspective view of the embodiment shown in FIG. 3.

As previously suggested, herein three major embodiments of the present invention are disclosed. A first, and most preferred, embodiment is depicted in FIGS. 2, 3 and 4. Referring to FIG. 2, the electrode 40 depicted therein is generally the same as electrode 1, FIG. 1. Electrode 40 includes an insulator construction 41, and a conductor member 42.

For the embodiment of FIG. 2, the insulator construction 41 includes first and second sections 44 and 45 which, together, define opposite sides 46 and 47 of the insulator construction 41. Each section 44 and 45 includes an elongate edge portion 50 and 51, respectively, FIG. 3. The edge portions 50 and 51 each include a border portion 52 and 53 (FIG. 3) respectively; the border portions 52 and 53 comprising a peripheral portion of each section 44 and 45, respectively, which extend along edges 50 and 51 respectively.

For the insulator construction 41 of FIGS. 2, 3 and 4, sections 44 and 45 are oriented to extend substantially parallel to one another, with edge portions 50 and 51 overlapping one another such that border portions 52 and 53 overlap. That is, a seam 60 is provided. By the term "substantially parallel" it is not meant that the sections 44 and 45 are necessarily precisely parallel. They may be out of precise coplanar alignment due, for example, to the thickness of the conductor member 42.

In general, electrode 40 is constructed such that a tab portion 61 of conuctor member 42 projects through seam 60 and over a portion of surface or side 46. As a result, FIGS. 2, 3 and 4, a pad portion 62 of conductor member 42 is positioned on one side 47 of insulator construction 41, and the tab portion 61 of conductor member 42 is positioned on an opposite side 46 of insulator construction 41. This leads to the advantages generally discussed above. It will be understood that except where tab portion 61 extends through seam 60, the seam may be sealed by means of an adhesive or the like.

In preferred embodiments, it may be desired to provide an outside seal over seam 60. This can be accomplished, for example, by placement of a strip 64 of adhesive tape or the like in overlap of seam 60, and partly extending over tab portion 61, transversely to a longitudinal extension thereof. Such a strip 64 will generally help seal seam 60 against leakage of foreign material thereinto, or leakage of conductive adhesive or electrolyte gel outwardly therefrom. The strip 64 is, of course, optional and is only shown in FIG. 2, and in FIGS. 3 and 4.

A significant advantage to the embodiment of FIGS. 2, 3 and 4 results from the overlap of sections 44 and 45. In particular, and referring to FIG. 3, should tab portion 61 be lifted relative to section 45, it will begin to pull against seam 60, and in particular edge 50, before it starts to lift pad portion 62 from a surface against which it is adhered. That is, the insultor construction 41 will tend to absorb any such stress placed on conductor member 42, before the stress is applied to the interface between the conductor member 42 and a user. Thus, good electrical communication is facilitated.

It will be understood that strip 64, to some extent, can facilitate this by providing that a first portion 67 (FIG. 2) of tab portion 61 adjacent or proximal to the pad portion 62 is adhered to insulator construction 41, in particular section 45. That is, tape 64 extends generally transversely along an extension of tab portion 61 between tip or tip portion 68 and section 67, securing region 67 in place. It will be understood that an alternate application would be with an adhesive positioned between section 67 and surface 47.

Referring to FIG. 4, electrode 40 is shown in exploded perspective as comprising: insulator construction 41 formed of sections 44 and 45 in overlap along edges 50 and 51, respectively; and, flat, flexible, conductive member 42 in position for extension of tab portion 61 outwardly from between sections 44 and 45, so that the pad portion 62 and tab portion 61 are oriented on opposite sides of insulator construction 41. For the embodiment of FIG. 4, section 67 of tab portion 61 is shown adhered in position to section 45, by means of double-stick tape strip 69. That is, adhesion in FIG. 4 between the tab portion 61 and section 45 is by means of adhesive underneath tab portion 61, rather than on top as shown in FIG. 2.

In FIG. 4, a field 70 of conductive adhesive is shown positioned generally underneath conductive member 42. It will be understood that in general the field 70 of conductive adhesive will be surrounded by a field, of skin adhesive also applied to insulator construction 41 the side thereof having pad portion 62 thereon. In FIG. 3 both the field 70 of the conductive adhesive and the field 71 of skin adhesive are viewable. In FIG. 4 the skin adhesive is not separately shown; however, it will be understood as applied, for example, in regions 71.

It is foreseen that in some embodiments the conductive adhesive 70 will be of a material which cannot be readily adhered to the skin adhesive; the skin adhesive typically being positioned on and completely covering side 47, including between 62 and insulator construction 44. For the preferred embodiment shown in FIG. 4, a layer 72 of scrim is positioned in between the conductive adhesive of field 70 and the skin adhesive. This layer 72 is generally formed of a material which can be readily adhered to both the skin adhesive and the conductive adhesive. For example, 8 pound tissue paper may be used in two sections, indicated at 73 and 74, FIG. 4.

In FIGS. 3 and 4, a layer of release liner 75 is shown positioned against that side of electrode 40 which has skin adhesive 71, conductive adhesive 70 and pad portion 62 thereon. Preferably, the release liner 75 will only directly contact skin adhesive or conductor adhesive (or spacer as described below).

In general, after manufacture and during storage, electrode 40 will be maintained with release liner 75 protecting the skin adhesive 71 and/or the field of conductive adhesive 70. It is foreseen that the release liner 75 will generally be stripped from the arrangement 40 immediately prior to use. A variety of release liners 75 may be utilized; for example, a liner comprising a polymer such as a polypropylene material, coated with a silicone release type coating which is readily separable from the skin adhesive and conductive adhesive. In some embodiments, it may be desired to place a spacer or tab 76 between release liner 75 and a portion of insulator construction 41, to facilitate the separation.

In FIG. 3, the arrangement of FIG. 4 and FIG. 2 (without strip 64 and with the release liner 75, spacer 76 and double-stick strip 69) is shown in cross section. The various components, including sections 44 and 45 having edges 50 and 51 and border portions 52 and 53 are readily viewable. In addition, the viewer can readily see the extension of flexible conductor member 42 through the insulator construction 41, leaving pad portion 62 on one side 47 and tab portion 61 on an opposite side 46.

It will be understood that the dimensions of the various layers, and their conformation during association, are shown somewhat exaggerated in FIG. 2, to facilitate an understanding of the invention. In general, an overall substantially flat appearance with only a very minor "s" type bend in the conductive member 42 is accommodated by the arrangement.

Figure 5:
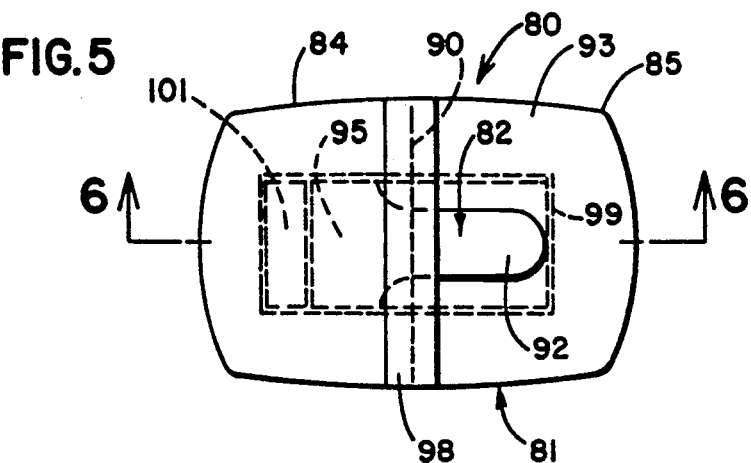
FIG. 5 is a top plan view of a first alternate embodiment of the present invention, shown with phantom lines indicating certain portions hidden from view.
Figure 6:
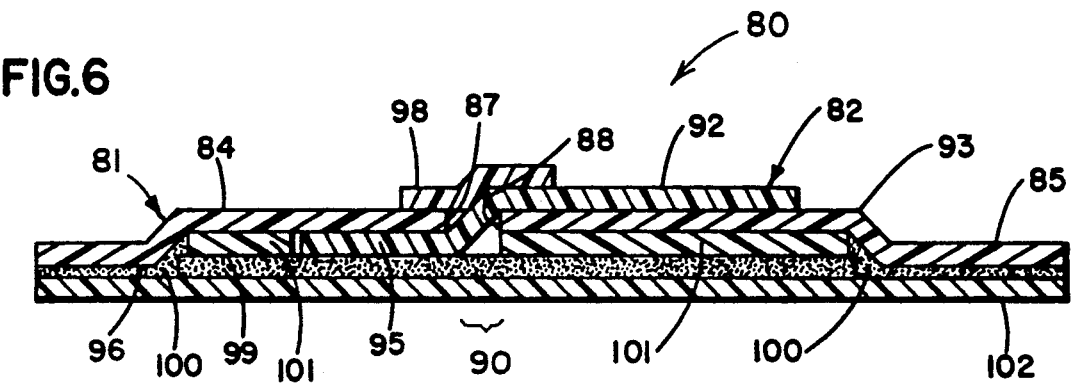
FIG. 6 is an enlarged side cross sectional view taken generally along line 6—6, of FIG. 5.

An alternate embodiment of the invention is depicted in FIGS. 5 and 6. Referring to FIG. 5, the electrode 80 depicted therein also includes an insulator construction 81 and a conductor member 82. The insulator construction 81 includes first and second sections 84 and 85, respectively. Referring to FIG. 6, each of sections 84 and 85 includes an edge 87 and 88, respectively. For the embodiment of FIGS. 5 and 6, instead of partly overlapping as with the embodiment of FIGS. 2, 3 and 4, sections 84 and 85 are substantially coplanar with one another (but for the relative thicknesses of conductor member 82 and the scrim), with edges 87 and 88 opposed to define a seam 90 therebetween. The flexible conductor member 82 can extend through seam 90, leaving tab portion 92 on one side 93 of the insulator construction 81, and pad portion 95 on an opposite side 96. For the embodiment of FIGS. 5 and 6, a strip 98 of adhesive tape or the like is shown extending over seam 90, to seal same. It will be understood that strip 98 also yields advantages analogous to strip 69 discussed with respect to FIG. 2, and generally concerning the prevention of stress against the interface of pad portion 95 with a user's body, as tab portion 82 is pulled away from side 93. It is noted that in FIG. 5, field 99 of conductive adhesive is depicted, and in FIG. 6 both field 99 of conductive adhesive and field 100 of skin adhesive are shown.

It will be understood that in many manners the embodiment of FIGS. 5 and 6 may be substantially the same as that of FIGS. 2, 3 and 4, including, if desired, analogous fields of conductive adhesives and skin adhesives; use of an analogous release liner; and, use of scrim 101 between the conductive adhesive and the skin adhesive. In FIG. 6, however, detail concerning certain such features is not shown, in order to facilitate an understanding of the major features relating to the relative constructions of the insulator construction 81 and the conductor member 82. In particular, no spacer is shown. A release liner 102 is, however, viewable.

Figure 7:
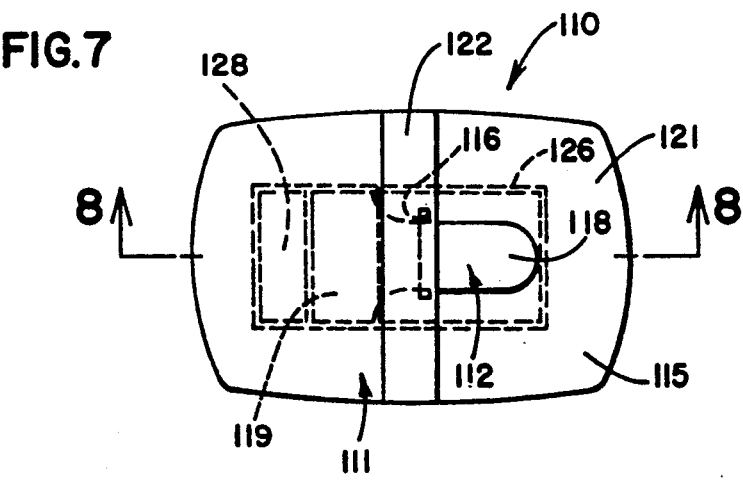
FIG. 7 is a top plan view of a second alternate embodiment of the present invention, shown with phantom lines indicating certain portions hidden from view.
Figure 8:
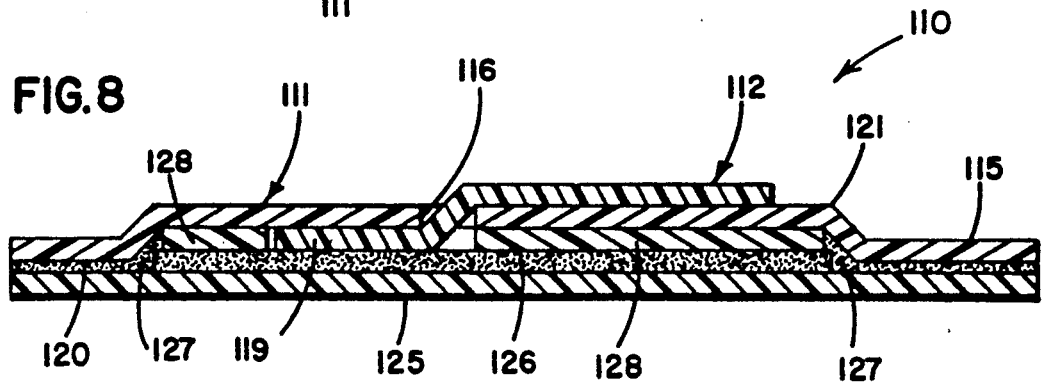
FIG. 8 is an enlarged side cross sectional view taken generally along line 8—8, FIG. 7.

Yet another embodiment of the present invention is depicted in FIGS. 7 and 8.

Referring to FIG. 7, the electrode 110 depicted therein includes an insulator construction 111 and a flat, flexible, conductor member 112. The insulator construction 111 includes a single section 115 of material having a slit or slot 116 positioned generally centrally therein. The slot 116 is sized to allow extension of a conductor member tab portion 118 therethrough. Thus, a pad portion 119 of conductor member 112 is positioned on one side 120 of the insulator construction 111 and the tab portion 118 extends along an opposite side 121. This will be further understood by reference to FIG. 8.

It will be understood that an optional strip 122, FIG. 7 of sealing tape or the like may be positioned over slot 116 and a portion of tab portion 118, in a manner generally analogous to that of previously discussed embodiments. The optional strip 122 of tape is shown in FIG. 7, but not in FIG. 8.

It will be further understood that the embodiment of FIGS. 7 and 8, except as discussed above, may be generally the same as that of the embodiments shown in FIGS. 2, 3 and 4 and also in FIGS. 5 and 6, respectively. That is, the arrangements can be manufactured and stored with a release liner 125 thereon (FIG. 8), fields (126 and 127, respectively) of conductive and skin adhesives may be similarly positioned; scrim (128) may be analogously used; and, a spacer (not shown) may be analogously positioned between the insulator construction 111 and the release liner; etc.

It is noted that for all three embodiments shown and described, the conductor member 42, 82 or 112 was depicted in substantially the same manner, i.e., as having a rather large, rectangular, pad portion with an elongate narrow tab portion extending outwardly therefrom. It will be understood that a variety of shapes may be utilized; however, the shape described is particularly efficient in that it provides for a good tab portion readily engagable by a clip, such as clip 7, FIG. 1, and it provides for a pad portion having a relatively large surface area, but which can be readily bordered on an outer periphery thereof by a border of insulator construction having skin adhesive thereon.

While a variety of materials may be utilized for the conductor member, such as conductor members 16, 42, 82 and 112, preferably the relatively flat, thin and flexible construction results from a material, such as a plastic material, having a silver/silver chloride conductive coating on at least one side thereof. If only one side of the conductor member has a conductive layer thereon, it will generally be that side which corresponds to the side of the pad portion projecting away from the insulator construction, and the portion of the tab portion facing the insulator construction.

It is foreseen that a typical conductor member will comprise a strip of material having a thickness of about 10–20 micrometers, such as Imperial ® lapping film No. 15 MIC LF S/C (3M Co., St. Paul, Minn.), having a coating of silver/silver chloride of about 0.3–0.7, and preferably about 0.5, micrometers thick thereon. It will be understood that such arrangements are not only flat, thin and flexible, but they will not be likely to render substantial shadows in X-rays. Thus, a patient wearing preferred biomedical electrodes according to the present invention can be subjected to X-ray tests without the need for removal (and accompanying discomfort and inconvenience) and reattachment of the biomedical electrode disclosed herein.

While a variety of shapes and sizes of conductor members may be used, preferred applications involve conductor members with pad portions about 1.5–2.3 cm by 1.0–1.4 cm and tab portions or tongues about 2.2–2.6 cm long by 0.8–1.2 cm wide.

A variety of materials may be utilized to form the substrate portion, i.e., the one or two main sections of the insulator construction. In general, what is preferred is a flexible material which will be comfortable to the user, and is relatively strong and thin. Preferred materials are polymer foams, especially polyethylene foams, non-woven pads, especially polyester non-wovens, and various types of paper. The most preferred materials are non-woven pads made from melt blown polyurethane fibre, which exhibit exceptional flexibility, stretch recovery and breathability. Melt blown polyurethane materials usable in insulator constructions in electrodes according to the present invention are generally described in U.S. application Ser. No. 193,906, filed May 13, 1988, and owned by applicant's assignee. Application Ser. No. 193,906 is incorporated herein by reference.

Preferred web materials (melt blown polyurethanes) for use in insulator constructions according to the present invention, have a web basis weight of about 60–140 g/m$^2$ (preferably about 120 g/m$^2$). Such materials have an appropriate tensile strength and porosity. A preferred porosity is about 100–300 grams water/m$^2$/24 hours (preferably 200 grams water m$^2$/24 hours) when tested according to ASTM E96-80 at 21° C. and 50% relative humidity. ASTM E96-80 is incorporated herein by reference. An advantage to such materials is that webs formed from them can be made which exhibit good elasticity and stretch recovery. This means that the electrode can stretch well, in all directions, with movement of the subject, without loss of electrode integrity and/or failure of the seal provided by the skin adhesive. Material with a stretch recovery of at least about 85%, in all directions, after stretch of 50% is preferred.

It will be understood that a variety of dimensions may be utilized for the biomedical electrode disclosed herein. Generally an insulator construction of about 3.5–4.5 cm by 5.5–6.5 cm will be quite suitable for typical foreseen applications. A thickness of about 400 to 600 micrometers provides for adequate strength and a desired low relief or profile, in typical applications.

It will also be understood that a variety of materials may be utilized as the skin adhesive. Typically, acrylate ester adhesives will be preferred. Acrylate ester copolymer adhesives are particularly preferred. Such materials are generally described in U.S. Pat. No. 2,973,826, incorporated herein by reference.

For the electrolyte layer, conductive adhesives such as those described in U.S. patent application Ser. No. 902,396 to Engel, owned by applicant's assignee and incorporated herein by reference, will be preferred. In particular, an adhesive according to Engel modified to the following ingredients is foreseen as a useful material:

|  | Dry Weight Percent |
|---|---|
| Copolymer: | |
| Acrylic Acid | 10.00 |
| N-vinyl pyrrolidone | 10.00 |
| Glycerin | 50.88 |
| Guar Gum | 0.12 |
| Water | 26.00 |
| Sodium hydroxide | 2.80 |
| Irgacure | 0.07 |
| TEGBM | .13 |
| | 100.00 |

The scrim can be fabricated from any of a number of materials. Generally, it is merely required that the material: have a reasonable tensile strength as a thin film; be flexible; and, form a good adhesive bond to both the conductive adhesive and the skin adhesive. Films of polyethylene, nylon and paper are usable, with Crystex Paper (Crystal Paper Co., Middletown, Ohio) being preferred.

Again, it will be understood that the previously recited examples are exemplary only of the invention, and the invention is not to be limited by the specific materials, dimensions, forms or arrangements described and/or shown in the drawings.

What is claimed and desired to be secured by letters Patent is as follows:

1. A biomedical electrode comprising:
   (a) an insulator construction having first and second opposite sides and including first and second sections of substantially non-conductive material, said sections each having an edge portion;
      (i) each of said first and second sections defining a portion of said insulator construction first and second opposite sides; and
      (ii) said first and second sections being oriented to extend substantially coplanar with one another, with said edge portions oriented opposed to one another, and in non-overlapping relationship to one another, to define a seam in said insulator construction; and
   (b) a conductor member having a pad portion and a tab portion;
      (i) said conductor member being oriented in said electrode with said pad portion positioned on said first side of said insulator construction, and with said tab portion positioned on said second side of said insulator construction, and said conductor member being oriented with a portion thereof projecting between said first and second section edge portions.

2. A biomedical electrode according to claim 1 wherein:
   (a) said insulator construction first side has a larger surface area than a first surface of said conductor member pad portion; said first side defining a border portion surrounding said conductor member pad portion; and, (b) said insulator construction second side has a larger surface area than a first surface of said conductor member tab portion; said second side defining a border portion surrounding said conductor member tab portion.

3. A biomedical electrode according to claim 2 including:
   (a) a layer of conductive adhesive on a side of said conductor member pad portion directed away from said insulator construction first side; and,
   (b) a layer of skin adhesive on said insulator construction first side, said layer of skin adhesive including a portion completely surrounding said layer of conductive adhesive.

4. A biomedical electrode according to claim 3, wherein
   (a) said insulator construction includes a polymeric plastic backing; and
   (b) said biomedical electrode includes a layer of scrim extending between at least a portion of said layer of conductive adhesive and at least a portion of said layer of skin adhesive.

5. A biomedical electrode according to claim 4, wherein
   (a) said polymeric plastic backing comprises a nonwoven pad of melt blown polyurethane fibre.

6. A biomedical electrode according to claim 1 including:
   (a) a strip of insulating tape positioned on said insulator construction second side and over said insulator construction seam.

7. A biomedical electrode according to claim 1, wherein
   (a) said conductor member comprises a strip of nonconductive plastic material having at least one side with a layer of conductive material adhered thereto.

8. A biomedical electrode according to claim 7, wherein
   (a) said conductor member has a conductive layer of silver/silver chloride on only one side thereof; said conductor member side having said conductive layer thereon comprising: a side of said pad portion directed away from said insulator construction first side; and, a side of said tab portion directed toward said insulator construction second side.

9. A biomedical electrode according to claim 1, wherein said insulator construction is flexible and wherein said conductor member is substantially flat and flexible.

* * * * *

UNITED STATES PATENT AND TRADEMARK OFFICE
CERTIFICATE OF CORRECTION

PATENT NO. : 5,133,355
DATED : July 28, 1992
INVENTOR(S) : Strand et al.

It is certified that error appears in the above-identified patent and that said Letters Patent is hereby corrected as shown below:

In Column 16, in the Table starting at Line 5, "Acrylic Acid" and "N-vinyl pyrrolidone" should be indented under "Copolymer".

Signed and Sealed this

Nineteenth Day of October, 1993

Attest:

BRUCE LEHMAN

Attesting Officer  Commissioner of Patents and Trademarks